United States Patent [19]

Esty et al.

[11] 4,311,145
[45] Jan. 19, 1982

[54] DISPOSABLE ELECTROSURGICAL INSTRUMENT

[75] Inventors: Janet M. Esty, Boulder; John A. Cox, Broomfield, both of Colo.

[73] Assignee: Neomed, Inc., Boulder, Colo.

[21] Appl. No.: 57,603

[22] Filed: Jul. 16, 1979

[51] Int. Cl.³ .......................................... A61B 17/39
[52] U.S. Cl. ............................................. 128/303.17
[58] Field of Search .................. 128/303.13–303.18, 128/800

[56] References Cited

U.S. PATENT DOCUMENTS

| | | | |
|---|---|---|---|
| 1,978,495 | 10/1934 | Landau | 128/303.16 |
| 3,920,021 | 11/1975 | Hiltebrandt | 128/303.17 |
| 3,955,578 | 5/1976 | Chamness et al. | 128/303.15 |
| 4,003,380 | 1/1977 | Wien | 128/303.17 |
| 4,005,714 | 2/1977 | Hiltebrandt | 128/303.17 |
| 4,016,881 | 4/1977 | Rioux et al. | 128/303.17 |
| 4,034,762 | 7/1977 | Cosens et al. | 128/303.17 |
| 4,170,234 | 10/1979 | Graham | 128/303.14 |
| 4,174,715 | 11/1979 | Hasson | 128/303.14 X |

FOREIGN PATENT DOCUMENTS 2734847  2/1979  Fed. Rep. of Germany ......................... 128/303.17

*Primary Examiner*—Lee S. Cohen
*Attorney, Agent, or Firm*—John E. Reilly

[57] ABSTRACT

A disposable instrument is adaptable for use in electrosurgical operations, such as, coagulation procedures used in blocking off fallopian tubes, and is characterized by having an improved electrode and switch assembly which permits interchangeable but permanent mounting of electrodes of a selected length and configuration within a handle grip. The electrodes conventionally may be of a type having normally spaced-apart tips which through actuation of a plunger disposed for extension through the handle grip will cause the tips to be brought together to grasp or surround the tube or other tissue to be coagulated. The interchangeable but positive connection of electrodes within the housing brings them into direct electrical connection with electrical contacts and specifically in such a way that the connection and mounting of the electrodes cannot be disturbed or broken. An improved control circuit for the instrument assures normal interruption of the electrical circuit to the electrodes unless the electrode tips have been advanced to the tube-engaging position as described. A switch in the sidewall of the housing is positioned with respect to the control circuit so as to permit positive movement in a direction establishing closure of the circuit into the electrodes only when the electrode tips are in the tube-engaging position.

23 Claims, 10 Drawing Figures

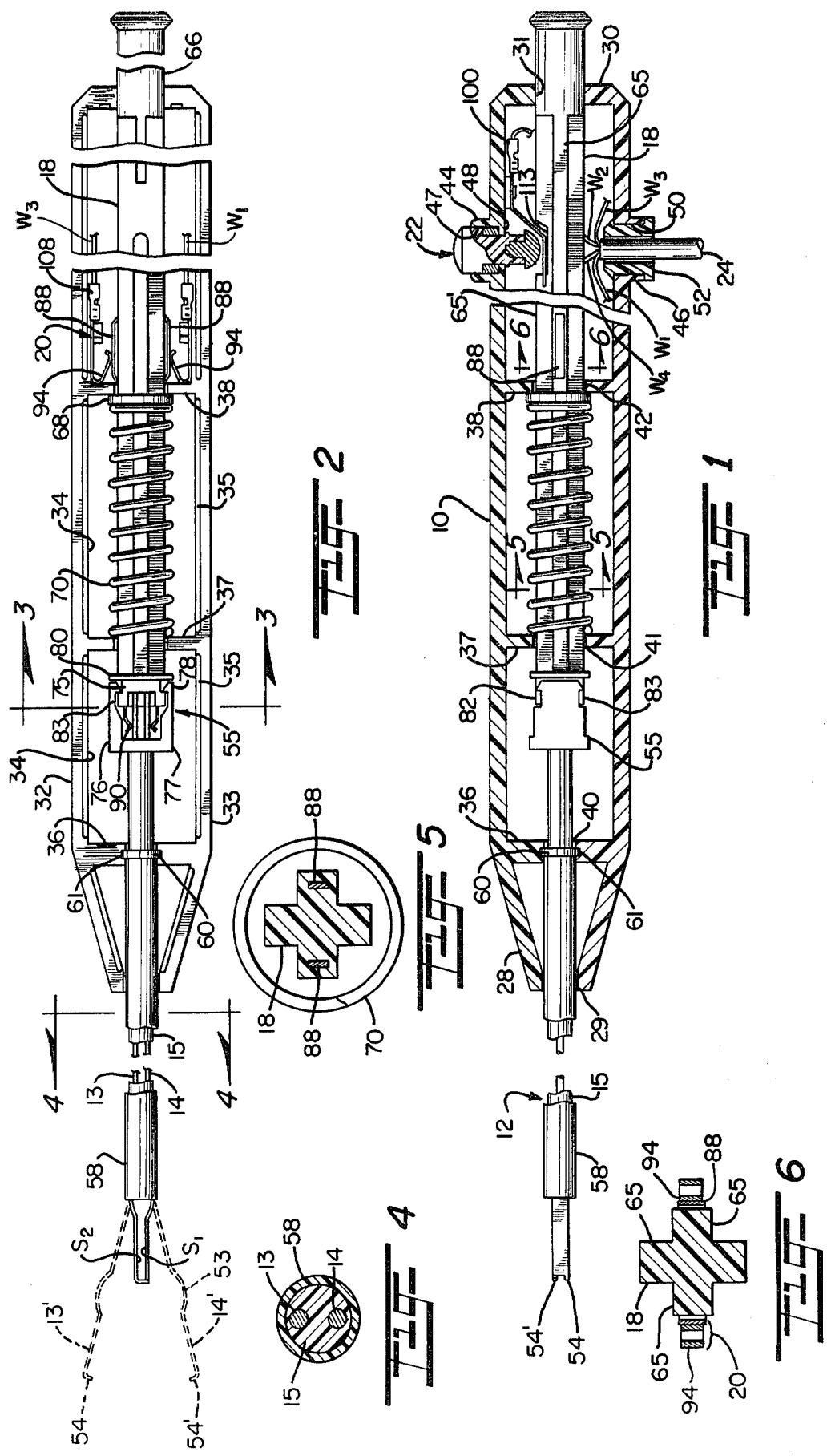

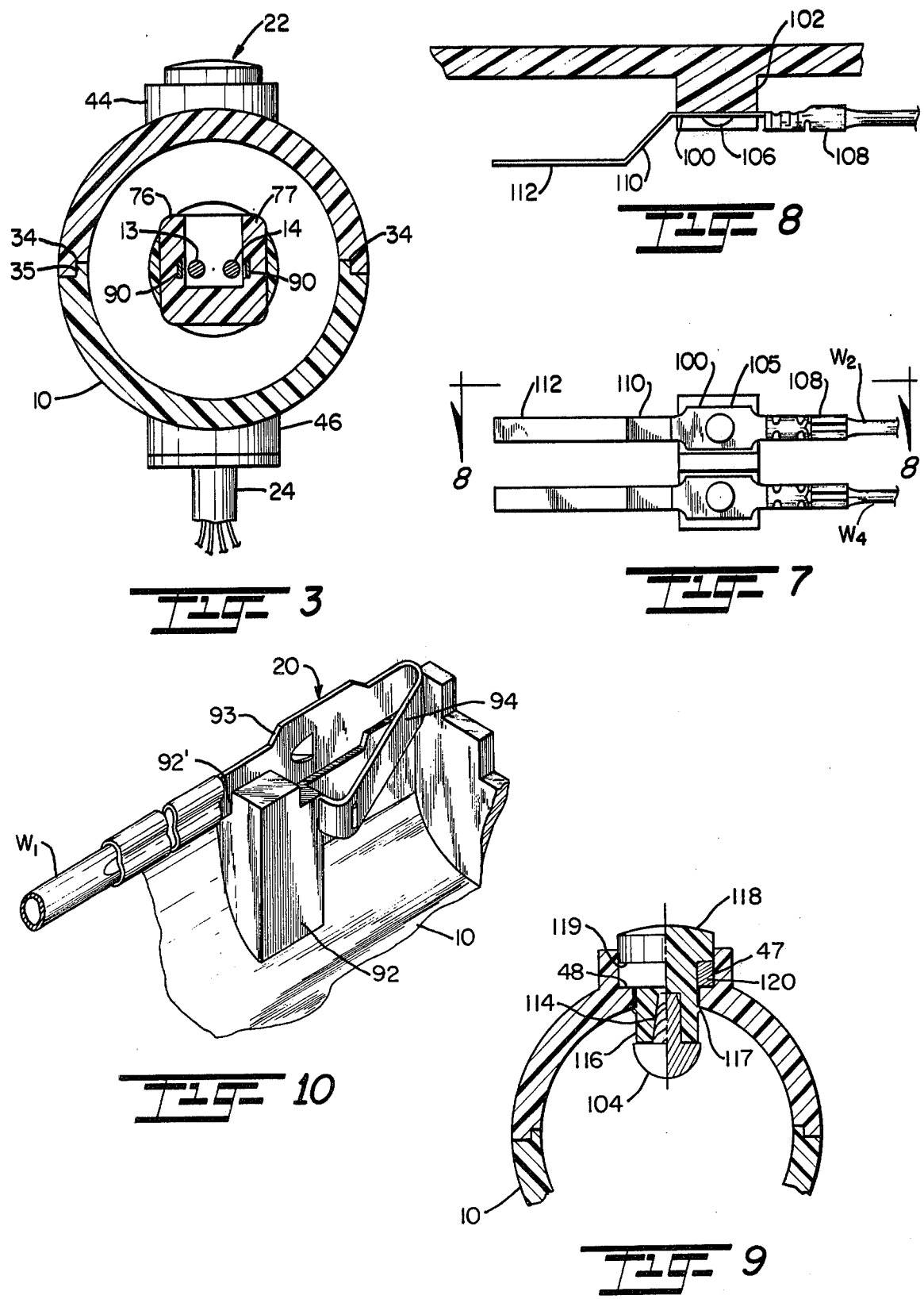

DISPOSABLE ELECTROSURGICAL INSTRUMENT

BACKGROUND OF THE INVENTION

Numerous types of instruments have been devised for performing laparoscopic tubal coagulation operations. Such instruments are broadly characterized by having a handle grip, a pair of electrodes supported on a probe element for extension from the grip and which electrodes terminate at their distal ends in a pair of tube engaging portions. An external power source leads into the handle grip and a foot or manually actuatable switch or button on the grip permits the operator to selectively apply current to the electrodes from the external power source. In performing tubal coagulation with a bipolar device, customarily the electrodes are passed through a trocar which has been inserted into the abdominal cavity, and the electrode tips are advanced to an open or spread-apart position so that they can be placed on opposite sides of the tube, after which the tips are advanced to a closed position in which the tube is engaged between the tips and current applied thereto for discharge between the electrodes tips so as to coagulate the tube. The same procedure is followed for each tube and may be repeated a number of times for each tube so as to assure complete coagulation and closure. Representative U.S. patents which disclose instruments of the type described are Rioux U.S. Pat. No. 3,938,527; and Bovie U.S. Pat. No. 1,813,902. Other U.S. patents of general interest pertaining to electrosurgical forcep instruments are Herman U.S. Pat. No. 1,731,069; and Bagley U.S. Pat. No. 3,100,489.

Further, laparoscopic instruments can either be categorized as monopolar or bipolar. In monopolar coagulation, a single electrode is energized and electric current is directed between the electrode and a dispersive pad or plate upon which the patient is placed. In bipolar instruments, the current discharge is between a pair of electrodes or electrode tips surrounding the tube thereby avoiding necessity of a dispersive pad or plate. Either in the use of the monopolar or bipolar laparoscopic instruments, it has been proposed in the past to employ a safety interlock or circuit breaker within the handle grip or housing to assure that there will be no electrical current delivered to the electrodes until they are properly positioned in surrounding relation to the tube to be coagulated. The safety interlock is interposed between the electrodes and cable so as to normally open or interrupt the circuit when the electrode tips are in the spaced-apart or spread position; and the circuit is closed so as to permit activation by the switch only when the electrodes are advanced to the tube grasping or closed position. It has also been proposed in various prior art monopolar and bipolar devices to provide for replaceable electrodes or tips so that the handle grip or housing portion of the instrument can be reused for a series of operations merely by replacing the electrodes and probe elements; or for different specific requirements different types of electrodes may be attached to the handle grip member, such as, to perform cutting and coagulation where needed.

Distinct problems arising with the use of the laparoscopic instruments of the type described, especially those having detachable or replaceable electrodes, are to maintain proper sterilization and cleaning, to avoid any possibility of poor electrical connections between the power source and electrodes during the course of an operation, and to establish and maintain a positive but releasable connection between the electrodes and electrode housing so as not to be subject to misalignment or loosening in use. Another drawback has been the placement of the manually activated switch for applying current to the electrodes so as to avoid accidental closure of the switch as the doctor is maneuvering and advancing the instrument into proper position for the operation to be carried out.

SUMMARY OF THE INVENTION

In accordance with the present invention, an electrosurgical instrument has been devised which is completely disposable; yet will permit the desired interchangeability of different electrodes in the process of assembling the instrument prior to its use without altering any other parts of the instrument. Thus one standard sized handle grip may be employed interchangeably with different selected sets of electrodes which are mounted in a probe or support member having the necessary means to firmly anchor the electrodes in place within the handle grip housing in such a way as to prevent misalignment of the electrode members in use or interruption in the electrical circuit from the external power source. A novel and improved form of control circuit has a dual safety interlock which will maintain an open circuit or circuit interrupt condition until the electrodes are advanced to a selected position, such as, for example in causing the electrode tips to be closed over a tube to be coagulated or cut. The circuit interrupt cooperates with a manually activated switch on the housing, the latter having a pushbutton member with a movable contact fully contained within a switch housing formed in the sidewall of the housing or handle grip of the instrument. An internal stop prevents movement of the pushbutton and activation of the switch until the electrode tips are advanced to the desired position, such as, the tube-engaging position as described.

Accordingly, it is a principal object of the present invention to provide for a novel and improved hand-operated, disposable instrument specifically adaptable for use in electrosurgery which is of simplified construction, highly efficient and reliable in use, and avoids a number of the drawbacks and disadvantages of prior art devices.

A further object of the present invention is to provide in an electrosurgical instrument for a novel and improved form of circuit interrupt which will avoid accidental delivery of current to an electrode assembly until the electrodes are in the proper position to perform the intended operation.

It is a further object of the present invention to provide for a novel and improved hand-operated, disposable tubal coagulation instrument which permits interchangeable but permanent installation of selected electrode members within a common handle and control assembly; and further wherein the handle control assembly is characterized by having a dual circuit interrupt to maintain an open circuit condition from an external power source into the electrodes until the electrodes are advanced to a preselected position for performing an operation.

An additional object of the present invention is to provide for a novel and improved switch actuator mechanism for use in combination with an electrosurgical instrument of the type having a slidable electrode assembly.

A still further object of the present invention is to provide for a novel and improved hand-operated, disposable instrument in which a selected set of electrodes are assembled into snap-fitting engagement within a handle grip housing and firmly anchored in place therein so as to be in direct electrical contact with a control circuit within the housing, yet be capable of slidable movement through the housing.

BRIEF DESCRIPTION OF THE DRAWINGS

Other objects, advantages and features of the present invention will become more readily appreciated and understood when taken together with the following detailed description in conjunction with the accompanying drawings, in which:

FIG. 1 is a side view partially in section of a preferred form of laparoscopic tubal coagulation instrument in accordance with the present invention;

FIG. 2 is a bottom view of the preferred form of invention shown in FIG. 1 with the lower housing removed;

FIG. 3 is a cross-sectional view taken about lines 3—3 of FIG. 2;

FIG. 4 is a cross-sectional view taken about lines 4—4 of FIG. 2;

FIG. 5 is a cross-sectional view taken about lines 5—5 of FIG. 1;

FIG. 6 is a cross-sectional view taken about lines 6—6 of FIG. 1;

FIG. 7 is an enlarged view in detail of the preferred form of switch contacts for the switch actuator mechanism of the present invention;

FIG. 8 is a cross-sectional view taken about lines 8—8 of FIG. 7;

FIG. 9 is an enlarged view in detail of the preferred form of pushbutton actuator in accordance with the present invention with the parts being shown partially in section; and FIG. 10 is a somewhat perspective view, enlarged of circuit interrupt contact used in the preferred form of invention.

DETAILED DESCRIPTION OF THE PREFERRED EMBODIMENT

Referring in detail to the drawings, there is shown in FIGS. 1 and 2 a preferred form of electrosurgical instrument which is broadly comprised of a holder or handle grip in the form of an elongated generally tubular housing 10, an electrode assembly 12 disposed for slidable movement within the holder and which is made up of a pair of electrodes 13 and 14 having electrode tips 13' and 14' mounted in a common probe 15 for forward extension through the holder 10 from detachable connection with an electrode plunger 18 which is slidably mounted within the holder. A control circuit from an external power source has a first circuit interrupt generally designated at 20 in FIG. 2, and a switch actuator is generally designated at 22 in FIG. 1. The external power source, not shown, is connected through a cable 24 to the circuit interrupt 20 and switch actuator mechanism 22 for the purpose of supplying electrical operating current to the electrodes 13 and 14. Generally, as illustrated in FIG. 2, the electrode assembly is capable of advancement between the retracted position shown in full and an extended position, shown dotted, in which the electrode tips 13' and 14' are free to spring outwardly into spread or spaced-apart relation.

Considering in more detail the construction and arrangement of the preferred form of invention, the housing 10 is of relatively thin-walled construction having a main tubular section which has a forward tapered end or nose portion 28 terminating in a central opening 29 at its leading edge. The rearward end of the housing terminates in a squared end wall 30 having a central opening 31 which is aligned with the opening 29 at the leading end. Preferably, the housing is made up of two symmetrical halves, the upper half being illustrated in the bottom plan view of FIG. 2. A description of the upper half of the housing will suffice for the lower half as well. Thus, each half comprises a thin-walled shell having diametrically opposed longitudinally extending edges 32 and 33 provided with inner, longitudinally extending recesses 34 along one edge 32 and correspondingly spaced ribs 35 along the opposite edge 33. The recesses 34 and ribs 35 mate with complementary recesses and ribs on the opposite half of the housing. A plurality of axially spaced, transversely extending, semi-circular locator or positioning members are formed in each semi-cylindrical half, there being a forward locator 36, intermediate locator 37 and rearward locator 38 at longitudinally spaced intervals which are aligned with correspondingly formed locators of the opposite half when the two halves are united together. In assembled relation, the front locator portions 36 define a common central opening 40 axially aligned with the central opening 29. Similarly, the intermediate locator 37 and rearward locator 38 have enlarged openings 41 and 42, respectively which are axially aligned with the central openings 29 and 40 and are sized to receive the electrode assembly 12. In addition, the wall of the housing is provided adjacent to its rearward end with a switch actuator housing 44 and a diametrically opposed cable housing 46 projecting radially and outwardly from the external surface of the housing 10. The housing 44 defines a generally cylindrical bore 47 with an inwardly stepped shoulder 48 flush with the inner wall surface of the housing. The housing 46 has a bore 50 of uniform diameter and which is adapted to receive a strain relief sleeve 52 which is positioned in pressfit surrounding relation to the cable 24 and encased electrical wires designated W1 to W4.

The electrode assembly 12 is constructed in a unique manner so as to permit interchangeable but positive, permanent connection of different selected types of electrodes 13 and 14 to the electrode control plunger 18. As shown in FIG. 1, 2 and 4, the electrodes 13 and 14 are molded in spaced parallel relation to one another within an insulating core 15 which defines the probe member. The core extends for the greater length of the electrode elements 13 and 14 such that the tips 13' and 14' are left exposed and project forwardly from the end of the core, each tip having an arcuate or outwardly bowed portion 53 adjacent to the leading extremity of the core. The electrode tips terminate in transverse, inwardly directed extremities 54 and 54' which extremities are offset with respect to one another so as not to contact one another when in the tube grasping position. The tips are coated with a dielectric insulating material except for uncoated or polished stainless steel electrical discharge surfaces $S_1$ and $S_2$ of limited area located on the inner surfaces of the tips to conduct electricity to the tube during coagulation in accordance with well-known practice. The opposite ends of the electrodes 13 and 14 project beyond the trailing end of the core into a first connector element 55 which is permanently affixed to and extends rearwardly from the trailing end of the core 15. An outer concentric sleeve 58 is disposed in surrounding relation to the core 15. This outer sleeve is slidable with respect to the core and is provided with an enlarged end 60 at its trailing end adapted to be inserted in close-fitting relation to an annular groove 61 in the front locator member 36 so that when the halves of the housing are assembled together the sleeve will be anchored in fixed relation to the housing. Accordingly, when the electrode plunger is in its retracted position as shown in full in FIG. 2, the outer sleeve 58 is dimensioned to be of a length to extend at least partially over the bowed portions of the tips in closely spaced substantially parallel relation to one another; however when the electrode assembly is advanced forwardly to the dotted line position shown in FIG. 2 the electrode tips 13' and 14' including the bowed portions will extend beyond the outer sleeve 58 and be free to spring outwardly into a spread-apart position. The sleeve 58 is also dimensioned to be of an external diameter such that it will be disposed in close-fitting relation to the front opening 29.

From a consideration of FIGS. 1, 2, 5 and 6, the electrode plunger 18 is in the form of an elongated rod-like member which is dimensioned to extend the greater length of the housing. As will be seen from the cross-sectional views of FIGS. 5 and 6, the body of the plunger disposed within the housing has radially extending ribs 65 extending lengthwise of the plunger to a point terminating adjacent to the rearward end wall 30 of the housing. The plunger includes a rearwardly projecting, generally cylindrical end portion 66 extending through the central opening 31 in the rear end wall 30 and which is manually engageable by the operator to depress or advance the piston forwardly through the housing. In the preferred form, there are a series of four longitudinal ribs 65 arranged at equally spaced circumferential intervals, or 90° apart. An annular disk 68 is mounted in fixed relation to the midsection of the piston internally of the housing to serve as a stop for one end of a compression spring 70 disposed in surrounding relation to the forward end of the plunger. When the plunger is assembled within the housing, the forward end of the compression spring 70 abuts the locator 37 and the stop 68 abuts the locator 38, and the spring is mounted under compression therebetween so as to bias the piston to a retracted position with the outer sleeve 58 retaining the electrode tips 13' and 14' in closely-spaced relation as described.

In order to permit positive snap-fitting interconnection between the probe and plunger members of the electrode assembly, the forward extremity of the piston 18 has a second connector 75 complementary to the first connector 55. Preferably the first connector 55 is of generally U-shaped configuration with opposite sides 76 and 77 extending in spaced parallel relation to one another and having inwardly facing groove portions or guideways 78 adjacent to the rearward free ends of the sides 76 and 77. The rearward ends of the electrodes 13 and 14 extend in spaced parallel relation to one another through the first connector and equidistant from opposite sides 76 and 77. The second connector 75 includes a flange 80 at the forward extremity of the body of the piston 18, and a forwardly projecting head portion 82 has diametrically opposed ribs 83 insertable laterally or in a transverse direction through the opposed grooves 78 in the first connector member such that the free ends of the sides 76 and 77 are situated between the ribs 83 and the flange 80.

In order to establish electrical contact between the electrodes 13 and 14 and the external power source which is applied through the lead wires W1 to W4, a pair of electrical contact strips 88 extend forwardly through the body of the piston from a point just rearwardly of the locator member 38, where the contact strips are exposed on the external surfaces of diametrically opposed rib members 65, forwardly to terminate in exposed wire clip elements 90, respectively, which project forwardly from the ribbed end of the second connector 75. Preferably, each of the electrical contact strips 88 is embedded within the body of the piston along its greater length from the spring clips 90 rearwardly to be exposed on the surface of a rib 65 just rearwardly of the locator member 38 and in aligned relation to the circuit interrupt contacts 20. As shown in FIG. 10, each circuit interrupt contact 20 comprises a conventional type of spring-loaded contact element of generally V-shaped configuration having one side 93 anchored to the internal wall of the housing by a slotted portion 92' in an abutment 92 on the inner wall surface of the housing. One contact 20 is spliced to a connecting wire designated W1 and the other contwact 20 is spliced to a wire W3 from the external power source; and an opposite free side 94 of each contact 20 is bent inwardly and spring-loaded so as to normally bear radially inwardly against an exposed portion of one of the contact strips 88.

The switch actuator mechanism as generally illustrated in FIG. 1 and shown in more detail in FIGS. 7 to 9 comprises a pair of contacts 100 anchored in closely-spaced parallel relation to one another on the internal wall surface of the housing as designated at 102. A movable pushbutton actuator 22 has an inner movable contact element 104 which when depressed in an inward radial direction will move into simultaneous contact with the spaced contacts 100 so as to establish electrical interconnection therebetween. Each of the contacts 100 as seen from a consideration of FIGS. 7 and 8 has a flat connecting end portion 105 having a limited aperture for insertion in pressfit relation of a lug or cylindrical projection 106 on the internal wall surface of the housing. The rearward end of the connecting end portion 105 is spliced as at 108 to one of the electrical power supply wires W2 W4 so as to complete the connection into the power source. From its point of connection to the housing, each contact 100 angles inwardly as at 110 into a longitudinally extending free end portion 112 aligned in inward radial spaced relation to the inner end of the contact 104. The free end portions 112 are located and aligned with the ribs 65 so as to flank opposite sides of a recessed area 113 in one of the ribs 65 and be normally spaced from the inner end of the contact 104.

Referring specifically to FIG. 9 when taken in conjunction with FIG. 1, the movable contact 104 is in the form of a one-way screw of the type referred to in the trade as a U-drive screw in which a tapered shank portion 114 is threaded into a counterbore at the inner end of the shank 116 of pushbutton 22. An enlarged head 118 at the external end of the pushbutton is of generally circular configuration and is sized to fit snugly within the cylindrical bore 47 formed by the housing 44 and has a shoulder portion 119 formed at the intersection of the head with the shank portion 16. A resilient washer 120 is seated within the bore 47 between the shoulder 119 of the pushbutton and the shoulder 48 of the housing for the purpose of normally maintaining the pushbutton and its movable contact 104 in spaced relation to the inner contact portions 112. A limit stop or annular ridge 117 is positioned intermediately along the external surface of the shank 116 in order to prevent accidental removal of the pushbutton member from the housing once assembled. Preferably the resilient washer 120 is composed of a spongy material such as a plastic foam which will readily yield when the pushbutton is depressed by the finger or thumb so as to permit the movable contact 104 to be advanced the necessary distance into engagement with the contact portions 112. Inward movement of the pushbutton will complete the circuit into the electrodes from the external power source only if the spring contacts 94 are aligned with and engaging the exposed surfaces 88 of the electrical contact strips and the recessed area 113 on upper rib 65' is aligned with the pushbutton to permit inward travel of the contact 104 into engagement with the free ends 112 which are disposed on the side surfaces of the ribs 65 transverse to the upper ribe 65'. When the pushbutton is released, the washer 120 will cause it to be returned to the normally open position as illustrated in FIG. 9 and in which position the rounded external surface of the head 118 will be substantially in the plane of the outer edge of the sidewall housing 44. Thus a definite inward force must be applied to the pushbutton to move the enlarged head 118 inwardly through the bore and through a distance of travel approximating one-third of the length of the bore to assure electrical connection between the movable contact 104 and the free ends 112 of the contacts 100.

In a typical procedure employing the preferred form of invention, the patient is first prepared in the customary manner for surgery and a small incision is made in the interior fold of the umbilicus following which a Verres cannula is inserted into the peritonial cavity for injection of $CO_2$. A trocar and cannula are then introduced into the cavity, the trocar removed, and laparoscope visualization instrument inserted through the cannula. A second trocar and cannula are introduced in the lower quadrant of the abdomen, the trocar is removed from the cannula, and the electrode probe section is inserted through the cannula into the cavity. Viewing the tube through the laparoscope, the surgeon then depresses the piston, bringing the electrode tips to their open or spread position, as shown in the dotted line position of FIG. 2. In this manner the tips may be aligned on opposite sides of the tube to be coagulated following which the electrode piston is released to return to the position as shown in full in FIG. 2 and such that the electrode tips in retreating through the sleeve 15 are contracted into a tube grasping position with the electrical discharge surfaces on the inner faces of the electrode tips contacting the tube. The control circuit is then closed by depressing the pushbutton 118 on the switch actuator mechanism 22 whereby a high frequency electrical operating current is applied from the external power source through the electrodes to coagulate the section of the tube which is clamped between the electrode tips. Upon release of the switch actuator, the procedure may be repeated the necessary number of times to assure complete coagulation and closure of the tube. Thereafter the same procedure as described above is followed for the other tube, following which the instrument is withdrawn and the wounds are closed.

In accordance with well-known practice, various different specific types of probes or electrodes may be interchanged or substituted for the electrodes described. For instance, electrodes capable of performing cutting or combined cutting and coagulation may be substituted. This is readily done in the assembly of the disposable instrument by mounting the desired set of electrodes 13 and 14 within the housing and detachably connecting the first connector end as described to the second connector or mating end of the electrode piston. Considering specifically the manner of assembly of the electrodes and housing, the desired set of electrodes is molded in place within the insulating core 15 so as to be disposed in spaced-apart, parallel relation to one another. The first connector end may either be molded simultaneously with the molding of the electrodes or otherwise permanently affixed to the end of the insulating core with the rearward ends of the electrodes 13 and 14 exposed within the hollow space formed between opposite sides 76 and 77 of the first connector end portion. The outer sleeve 58 is then advanced over the insulating core to the position shown in full in FIG. 2 and with the enlarged end 60 facing but in adjacent spaced relation to the first connector end. The probe assembly as described is then detachably connected to the electrode piston by laterally inserting the ribbed portions 83 on the second connector into the slots 78 on the first connector until the exposed electrode ends 13 and 14 abut the inner wall of the cavity formed in the ribbed end portion 83 and are stationed between the inwardly bent extremities of the spring clips 89. The electrode assembly is then inserted into one of the housing halves, for example as illustrated in FIG. 2, with the enlarged end 60 of the outer sleeve 58 inserted into the slot 61 of the front locator 36 and the compression spring 70 mounted under compression between the locators 37 and 38. Further the electrode assembly is turned or rotated with respect to the housing such that the exposed surfaces of the electrical contact strips 88 are aligned with the spring contacts 94 of the circuit interrupt 20 in order to establish direct electrical contact therebetween. The mating halves of the housing are then brought together with the locator ribs on one half advanced into registry with the inset or slotted portions 34 of the complementary half. The halves may be united by ultrasonic welding, a suitable adhesive or bonding material applied to the confronting edges 32 of the halves or by snap-fitting the halves together so that when the halves are closed they will be joined into a unitary housing.

In assembled relation, the disposition of the probe element as described specifically with the outer insulating sleeve 58 fixed in position within the front locator 36 and further supported by the surrounding edge of the front opening 29 will prevent any accidental displacement or loosening of the detachable connectors between the probe and piston members; and the probe will be maintained in accurate axial alignment with the longitudinal axis of the piston so as to be responsive to advancement of the piston through the housing in forcing the electrode tips into the spread position.

All of the elements of the disposable instrument as described may be composed of non-toxic plastic materials, such as, ABS or polycarbonate materials, with the exception of the electrically conductive materials. Preferably the insulating core 15 is composed of a rigid non-toxic plastic material and the outer insulating sleeve is composed of Nylon. The entire instrument is extremely lightweight and relatively inexpensive to manufacture and assemble so that once the operation is completed the entire instrument may be discarded. It is emphasized in this connection that the instrument housing is intentionally assembled over the electrode probe so as to prevent substitution or interchange of the probe element once assembled.

Although the present invention has been described with particularity relative to the foregoing detailed description of a preferred embodiment, various modifications, changes, additions and applications other than those specifically mentioned herein will be readily apparent to those having normal skill in the art without departing from the spirit and scope of this invention.

We claim:

1. In an electrosurgical apparatus wherein an electrode assembly is slidably mounted in a holder, the assembly having at least one electrode element projecting forwardly from one end of said holder to terminate in an element tip end which is operative to discharge electrical current applied thereto and further having a plunger at the end of said electrode element opposite to said tip end disposed within said holder for selective slidable advancement of said electrode element between an extended and retracted position, there being control circuit means disposed in said holder for selectively applying electrical operating current to said electrode element, the improvement comprising:

first and second connector members between one end of said plunger and said opposite end of said electrode element detachably interconnecting said electrode element and said plunger in axially aligned, end-to-end relation to one another;

said control circuit means including a first electrical lead projecting from said one end of said plunger and said electrode element including a second electrical lead projecting from said opposite end of said electrode element and movable into direct electrical contact with said first electrical lead when said first and second connector members are detachably connected together;

an outer electrically insulated sleeve disposed in surrounding relation to said electrode element along its substantial length, said sleeve having one end terminating adjacent to said electrode element tip end and an opposite end terminating adjacent to said opposite end of said electrode element; and said holder including positioning means therein engageable with said opposite end of said sleeve whereby to anchor said sleeve with respect to said holder while supporting said electrode element in axially aligned relation to said plunger, and resilient means normally urging said electrode element into the retracted position with respect to said sleeve.

2. In an electrosurgical apparatus according to claim 1, one of said first and second connector members being laterally inserted into detachably connected relation to the other of said first and second connector members, each of said connector members having a central aperture and each of said first and second electrical leads projecting into one of said apertures.

3. In an electrosurgical apparatus according to claim 1, said positioning means being defined by an annular locating rib in said holder and a ring-like member interposed between said locating rib and said opposite end of said sleeve.

4. In an electrosurgical apparatus according to claim 3, said ring-like member affixed to said opposite end of said sleeve and being inserted in a slot formed in said locating rib.

5. In an electrosurgical apparatus according to claim 2, said first and second connector members defined by mating, diametrically opposed ribs and slotted portions, respectively, said diametrically opposed ribs laterally inserted into said diametrically opposed slotted portions to detachably interconnect said electrode element and plunger in end-to-end relation to one another.

6. In an electrosurgical apparatus according to claim 1, said control circuit means including an electrical contact strip extending through the interior of said plunger and terminating in said first electrical lead at one end of said plunger.

7. In an electrosurgical apparatus according to claim 1, said holder being of elongated, generally tubular configuration and including a plurality of axially spaced plunger locator members centering said plunger within said holder, said plunger projecting through one end of said holder opposite to said electrode element, said resilient means mounted under compression on said plunger for extension between a pair of adjacent plunger locator members to normally urge said plunger in a rearward direction causing said sleeve to be in its forwardmost position with respect to said electrode element tip end.

8. In an electrosurgical apparatus according to claim 7, said control circuit means including at least one fixed electrical contact member on said holder and an electrical contact strip on said plunger normally disposed in direct electrical contact with said fixed electrical contact member on said holder when said sleeve is in its forwardmost position with respect to said electrode element tip end and movable away from electrical contact with said fixed electrical contact member when said plunger is urged in a direction overcoming said resilient means.

9. In an electrosurgical apparatus according to claim 1, said holder being of elongated generally tubular configuration and said control circuit means including a pair of switch contacts mounted in fixed relation to the interior of said holder, pushbutton actuator means disposed in a sidewall housing in said holder, said sidewall housing defining a cylindrical bore through which said pushbutton actuator means, extends, said pushbutton actuator means including a movable contact element disposed for extension through said bore into the interior of said housing into contact with said switch contacts to establish an electrical connection therebetween, and biasing means in said sidewall housing normally urging said pushbutton actuator means to a position maintaining said movable contact element away from contact with said switch contacts.

10. In an electrosurgical apparatus according to claim 9, said sidewall housing having an inwardly stepped shoulder at the inner end of said cylindrical bore, said pushbutton actuator means being in the form of an enlarged end portion on said movable contact element and said biasing means defined by a resilient cushion interpositioned between said inwardly stepped shoulder and said enlarged end portion.

11. In an electrosurgical apparatus according to claim 10, said plunger having longitudinally extending ribs and a recess in one of said ribs movable into alignment with said pushbutton actuator means, said pair of switch contacts disposed on opposite sides of said pushbutton actuator means and engageable by said movable contact element only when said recess is aligned with said pushbutton actuator means.

12. A disposable laparoscopic instrument adaptable for use with a high frequency electrosurgical generator having a power source, said instrument comprising:

an elongated probe including an elongated core composed of electrical insulating material and a pair of electrodes extending longitudinally through said core in closely spaced parallel relation to one another, said electrodes terminating in a pair of electrode tips and a first complementary connector member at the end of said core opposite to said electrode tips, the ends of said electrodes opposite to said electrode tips being exposed within said first complementary connector member;

an electrode slide member having a second complementary connector member at one end of said slide member complementary to said first complementary connector member, high frequency conducting means for connection to said power source extending through said slide member and terminating in an electrode contacting end portion disposed in said second complementary connector member and movable into direct electrical connection with said electrodes when said first and second complementary connector members are interconnected together, said high frequency conducting means extending from said electrode contacting end portion and terminating in contact strips on the external surface of said slide member;

a handle comprising a hollow elongated shell provided with openings at opposite ends thereof, said probe extending through the opening at one end of said shell and connected in end-to-end relation to said slide member, said slide member having a manually engageable extension projecting externally through the opening at the opposite end of said shell, and switching means on said shell connectable to said power source and high frequency conducting means having first and second inner stationary contacts disposed in axially spaced relation to one another on the inner wall of said shell, said first contacts engageable with the contact strips of said high frequency conducting means and said second stationary contacts projecting radially and inwardly from the inner wall surface of said shell, a manual pushbutton having a movable contact projecting radially through the sidewall of said shell and into position spaced from said second stationary contacts and an extended position engaging said second stationary contacts, said electrode slide member including switch interrupt means movable between a first position permitting electrical connection between said movable contact on said pushbutton and said second stationary contacts and a second position in which said switch interrupt means prevents movement of said movable contact to the extended position.

13. A disposable laparoscopic instrument according to claim 12, said elongated probe including an outer insulating sleeve slidably mounted on said insulating core, said sleeve anchored with respect to said handle and having a distal end portion normally embracing said electrode tips to maintain them in a retracted position when said slide member is in a position establishing connection between said conducting means and said first stationary contacts, said electrode tips and elongated probe being slidable forwardly through said insulating sleeve when said electrode slide member is advanced to the second position whereby said electrode tips are free to spring outwardly to a spread position.

14. A disposable laparascopic instrument according to claim 12, said switch interrupt means defined by a generally rib-shaped portion on said electrode slide member provided with a recess therein, said second stationary contacts extending from the inner wall of said shell alongside said recess, and said movable contact movable into said recess into engagement with said second stationary contacts when said electrode slide member is disposed in the first position.

15. A disposable laparoscopic instrument according to claim 12, said tips projecting beyond one end of said core and having arcuate portions bowed transversely away from the longitudinal axis of the electrodes at a point just beyond the end of the core, said arcuate portions being bowed in opposite transverse directions away from one another.

16. A disposable laparoscopic instrument according to claim 12, said first and second connnector members having interfitting ribs and slots in which said ribs are laterally inserted into said slots.

17. In a bipolar laparoscopic instrument wherein an electrode assembly is slidably mounted in a holder, the assembly having a pair of electrodes projecting forwardly from one end of said holder to terminate in tip ends which are operative to discharge electrical current applied thereto and further having a plunger at the end of said electrodes opposite to said tip ends disposed within said holder for selective slidable advancement of said electrodes between an extended and retracted position, there being control circuit means disposed in said holder for selectively applying electrical operating current to said electrodes, the improvement comprising:

male and female connector members between one end of said plunger and said opposite end of said electrodes detachably interconnecting said electrodes and said plunger in end-to-end relation to one another, one of said male and female connector members being laterally inserted into detachably connected relation to the other of said male and female connector members, each of said male and female connector members having a central aperture into which first and second electrical leads are extended therein;

said control circuit means including first electrical leads projecting from said one end of said plunger and second electrical leads projecting from said opposite end of said electrodes and movable into direct electrical contact with said first electrical leads when said male and female connectors are detachably connected together;

an outer electrically insulated sleeve disposed in surrounding relation to said electrodes along their substantial length, said sleeve having one end terminating adjacent to said electrode tips and an opposite end terminating adjacent to said opposite end of said electrodes; and said holder defined by a pair of symmetrical halves joined together into a unitary assembly including positioning means therein engageable with said opposite end of said sleeve whereby to anchor said sleeve with respect to said holder while permanently mounting said electrodes in axially aligned relation to said plunger.

18. In a bipolar laparoscopic instrument according to claim 17, said positioning means having an annular locating rib in said holder, and said sleeve having an enlarged end portion at said opposite end positively engaged with said locating rib.

19. In a bipolar laparoscopic instrument according to claim 17, said male and female connector members defined by mating, diametrically opposed ribs and slotted portions, respectively, said diametrically opposed ribs laterally inserted into said diametrically opposed slotted portions to detachably interconnect said electrodes and plunger in end-to-end relation to one another.

20. In a bipolar laparoscopic instrument according to claim 17, said control circuit means including electrical contact strips extending through the interior of said plunger and terminating in said first electrical leads at one end of said plunger.

21. In a bipolar laparoscopic instrument according to claim 17, said holder being of elongated, generally tubular configuration divided into semi-cylindrical halves along the longitudinal axis thereof and including a plurality of axially spaced plunger locator members centering said plunger within said holder, said plunger projecting through one end of said holder opposite to said electrodes, resilient means mounted under compression on said plunger for extension between a pair of adjacent plunger locator members to normally urge said plunger in a rearward direction causing said sleeve to be in its forwardmost position with respect to said electrode tips.

22. In a bipolar laparoscopic instrument according to claim 21, said control circuit means including at least one fixed electrical contact member on said holder and an electrical contact strip on said plunger normally disposed in direct electrical contact with said fixed electrical contact on said holder when said sleeve is in its forwardmost position with respect to said electrode tips and movable away from electrical contact with said fixed electrical contact member when said plunger is urged in a direction overcoming said resilient means.

23. In a bipolar laparoscopic instrument according to claim 17, said holder being of elongated generally tubular configuration divided into semi-cylindrical halves including a pair of switch contacts mounted in fixed relation to the interior of said holder, a pushbutton actuator disposed in a sidewall housing in said holder, said sidewall housing defining a cylindrical bore through which said pushbutton actuator extends, said pushbutton acutator including a movable contact element disposed for extension through said bore into the interior of said housing into contact with said switch contacts to establish an electrical connection therebetween.

* * * * *